United States Patent
Bolz et al.

[11] Patent Number: 5,964,794
[45] Date of Patent: Oct. 12, 1999

[54] IMPLANTABLE STIMULATION ELECTRODE

[75] Inventors: Armin Bolz; Ronald Froehlch, both of Erlangen; Martin Stelzle, Reutlingen; Johannes Schmitt, Bad Camberg; Anke Diederich, Mainz; Thorsten Cassier, Idstein; Roland Wagner, Berlin, all of Germany

[73] Assignees: Biotronik Mess- und Therapiegeraete GmbH & Co. Ingenieurbuero Berlin, Berlin; Max-Planck-Gensellschaft zur Foerderung der Wissenschaften e.V. Berlin, Munich, both of Germany

[21] Appl. No.: 08/821,292

[22] Filed: Mar. 20, 1997

[30] Foreign Application Priority Data

Mar. 21, 1996 [DE] Germany .......................... 196 13 002
Jul. 19, 1996 [DE] Germany .......................... 196 30 563

[51] Int. Cl.[6] ................................................ A61N 1/05
[52] U.S. Cl. ................................... 607/121; 600/373
[58] Field of Search ............................ 607/119, 120, 607/121, 116; 600/372, 373, 374

[56] References Cited

U.S. PATENT DOCUMENTS 4,552,625  11/1985  Van Der Velden .
5,080,099   1/1992  Way et al. .
5,324,324   6/1994  Vachon et al. .

FOREIGN PATENT DOCUMENTS

0388480A1   9/1990  European Pat. Off. .
0453117    10/1991  European Pat. Off. .
249635A1    9/1987  German Dem. Rep. .
251079A1   11/1987  German Dem. Rep. .
2842318A1   4/1980  Germany .
4322130A1   1/1995  Germany .
4334272A1   4/1995  Germany .
WO91/15250 10/1991  WIPO .
93/02739    2/1993  WIPO .

OTHER PUBLICATIONS

"Optimisation of ensyme electrodes" by L.X. Tang et al. vol.B18–B24 of MBEC Biosensors special feature, May 1990.

Max Schaldach: "Electrotherapy of the Heart— Technical Aspects in Cardiac Pacing". Springer Verlag, 1992, pp. 145–190.

*Primary Examiner*—Scott M. Getzow
*Attorney, Agent, or Firm*—Spencer & Frank

[57] ABSTRACT

An implantable stimulation electrode for use with an implantable tissue stimulator, in particular a pacemaker, defibrillator, bone or neurostimulator, having a metal substrate body and a coating, applied to the substrate body, for reducing the electrode impedance and/or increasing the tissue compatability, in which a ultrathin, specifically functionalized organic coating forming the entire outer surface of the stimulation electrode is provided, which adheres to the underlying surface as a consequence of irreversible physisorption or covalent chemical bonding.

20 Claims, 7 Drawing Sheets

IMPLANTABLE STIMULATION ELECTRODE

The invention relates to an implantable stimulation electrode of the type defined by the preamble to claim 1.

Electrodes for stimulating body tissue by electrical stimulation are known in great variety. Although metal materials, because of the requisite good conductivity, are used by far the most often to transmit electrical currents to living tissue—as to other objects—electrodes are also known in which elements of conductive polymers are contemplated; see for instance U.S. Pat. No. 5,080,099, in which skin electrodes with hydrogel contact elements are described as stimulation electrodes for an external defibrillator and/or pacemaker.

In the rapid development of the technology of implantable pacemakers and defibrillators, great attention has also been paid to refining the design and to the optimal choice of material for the associated implantable electrodes. A summary of the physical-chemical principles to be noted in this respect as well as references to important developments both with respect to pacemaker electrodes and to biocompatible materials from this standpoint of pacemaker technology through the beginning of the 1990s (including extensive sources) is found in M. Schaldach: Electrotherapy of the Heart—Technical Aspects in Cardiac Pacing, Springer 1992, pp. 145–190.

For the utility of an implantable stimulation electrode—especially one intended for long-term use in a tissue stimulator with a nonrenewable energy source and that must therefore contribute to requiring only minimal energy—a high electrode capacitance and hence low electrode impedance and the greatest possible degree of biocompatability are of prevailing importance.

Implantable stimulation electrodes that are sophisticated along these lines are described for instance in European Patent Disclosure EP 0 453 117 A1 or International Patent Disclosure WO 93/02739. The first of these references describes a multilayer electrode structure with a platinum base body compressed from fiber or wire material, an adhesive layer, a platinum, carbon or aluminum texturizing layer with a rough surface, and a catalytically acting platinum or platinum/carbon cover layer. In the latter reference, a stimulation electrode of substantially simpler design is described, which because of an inert coating with a fractal surface structure has a very large active surface area. In an advantageous version, this electrode comprises a titanium base body with an iridium, iridium nitride, or iridium oxide coating.

Even with extensively optimized electrodes of this last type, a temporary increase in the stimulation threshold occurs after implantation because of tissue irritation; in this phase, this leads to increased energy consumption on the part of the stimulator, and under some circumstances—depending on the type of device—necessitates complicated adjustment corrections.

From U.S. Pat. No. 4,552,625, a reference electrode encapsulated in an open-cell polymer matrix filled with a special liquid is known, which is intended for measurement arrangements for in vivo determination of the pH value. This electrode is not a stimulation electrode, nor can it be used as such.

The object of the invention is to disclose an implantable stimulation electrode of the type referred to at the outset, with which tissue irritation after implantation and especially an attendant rise in the stimulation threshold can be avoided.

This object is attained by a stimulation electrode having the characteristics of claim 1.

The invention encompasses the concept of providing an organic layer on the surface of an implantable stimulation electrode, which layer prevents or at least decisively reduces the nonspecific adsorption of biological macromolecules and is selectively specifically functionalized or functionalizable. Such an effect, which leads to a novel quality of biocompatability while simultaneously obtaining high phase-boundary capacitance and hence low electrode impedance, is unattainable with the known stimulation electrodes having a metallic or inorganic surface. The term "organic layer" will be used hereinafter to include such a layer having silicon atoms, of the kind that can be formed by reaction with silanes, for instance. An additional functionalization of potential practical significance is that the organic layer has sensor molecules (such as enzymes) such that the stimulation electrode can act as a biosensor electrode.

In a further important functionalization, the organic layer has a medicinal active ingredient, in particular an antiinflammatory medication, which can be exported from the organic layer under diffusion or solution control. In particular, the medicinal active ingredient may be substantially embedded between constituent layers of the multilayer structure.

The organic layer is ultrathin; that is, its layer thickness of the organic coating is in the range between 1 and 200 nm, and in certain versions (for instance as a polyelectrolyte multilayer) is preferably in the range between 3 and 50 nm.

To assure advantageous electrical properties, and especially little influence on the high phase-boundary capacitance of highly sophisticated stimulation electrodes, even at relatively high layer thicknesses in the aforementioned range, the organic layer in an advantageous embodiment is embodied such that it has a relative dielectric constant of greater than 100 and in particular greater than 300. At very slight layer thicknesses, layers with a relatively low dielectric constant can also be used.

In one feature of the concept of the invention, the organic coating has a polymeric network structure formed by substantially lateral polymerization; in other feature, it is covalently bonded to the underlying surface. A combination of the two layer-forming mechanisms is also possible.

For the functional modification of the electrode surface, two fundamental surface modification methods may be employed:

1. Multistage a) Modification of the surface with still-reactive substance layers with thicknesses in the nanometer range, the substances being fixed to the surface by means of chemical bonding or "mechanical" anchoring (physisorption). The applied low-molecular or polymeric substance layers preferably have the following reactive structures:

—$RNH_2$, —$RN(H)alkyl$, —$RCH=CH_2$, —$RC\equiv CH$,
—$RC\equiv CR$—, —$RCHO$ (aldehyde), —$RCH_2hal$, —$RCH_2SH$,
—$RCH_2OH$, —$RCH(OH)R$—, $RC(O)hal$ (acid halide),
—$RN=C=O$, $RSiH_2$, —$RSO_2hal$, b) Further reaction of the reactive structure with suitable hydrophilic components whose basic structure is [K]-[hydrophil], in which [K] preferably stands for and [hydrophil] preferably stands for polyoxyalkylene units, especially preferably formed on the basis of ethylene oxide or propylene oxide or mixtures thereof.

It is within the scope of the invention that the hydrophilic polyoxyalkylene units are terminated with hydroxyl groups (—OH), short-chained oxyalkyl groups (such as —OCH$_3$, —OCH$_2$CH$_3$, —OCH(CH$_3$)$_2$) or amino groups (such as —NH$_2$). It is also within the scope of the invention that the polyoxyalkylene units are substituted with hydroxyl-terminated alkyl structures. It is also possible to hydrophilize the polyoxyethylene units additionally with secondary hydroxyl groups, for instance on the basis of glycidol. The ideal structure is:

The size of [hydrophil], that is, the mean number of oxyalkyl units or hydroxyl positions per bonding location can very easily be adapted to the intended use. It may suffice to provide one hydrophilic unit (oxyalkylene, hydroxyl), while conversely in certain cases it is expedient to chemically fix up to 100 units or more to the surface. Usually from 3 to 20 and preferably 5–10 units per chemical bonding location are fixed.

The surface density of reactive structures from paragraph a) is not critical. The size (molecular weight) of [hydrophil] can easily be adapted to the existing anchoring density. A low density of reactive structures in accordance with step a) can be compensated for by the chemical fixation of especially large [hydrophil] blocks, without worsening the protein-repellent properties. If there is a high density of reactive structures, then complete coverage is attained even with small [hydrophil] units.

It is also within the scope of the invention that in the reaction of the reactive structure of a) with the hydrophilic component [K]-[hydrophil], a branched overall structure is formed, if the hydrophilic component has the structure [hydrophil]1-[K]-[hydrophil]$_2$.

The choice of partners for reaction steps a) and b) is made on the one hand with a view to the intended type of anchoring to the surface and on the other the intended type of bonding between the first, still-reactive substance layer and the substructure [K].

Preferred principles for linking between the still-reactive first substance layer and [K] are the following:
  alkylation of amines with epoxies and alkyl halides
  synthesis of Schiff's bases/enamines of primary/secondary amines and aldehydes
  synthesis of carboxylic acid esters/carboxylic acid amides of carboxylic acid anhydrides/carboxylic acid halides/lactones and hydroxyl/amine derivatives
  synthesis of sulfonic acid esters/sulfonamides of sulfonic acid halides and hydroxyl/amine derivatives
  synthesis of carbamic acid and urea derivatives of isocyanates and hydroxyl/amine derivatives
  synthesis of sulfides from alkyl halides and sodium sulfide or alkyl halides and thiols
  synthesis of disulfide bridges
  Si—C bond linkage by catalytic or radical hydrosilylation of alkenes or alkines with H—Si— functionalized compounds.

Details of the synthesis operations can be learned from the relevant chemical professional literature (such as Organikum, 17th Edition, VEB Deutscher Verlag der Wissenschaften, Berlin 1988; B. Marcinec, Comprehensive Handbook on Hydrosilylation, First Edition, Pergamon Press 1992).

2. Single-stage

It may be preferable for already hydrophilically functionalized components to be applied to the substrate surface in one step. In this connection, hydroxyl- or polyoxyalkyl-functionalized halogen or alkoxysilanes prove to be valuable. The choice of mono-, di- or tri-functionalized silanes and also the application technology (such as gas phase coating, immersion coating) is made as a function of the vapor pressure and the chemical nature of the substrate underlay.

In an advantageous version, the organic coating has a multilayered structure formed by successive adsorption of one anionic and one cationic polyelectrolyte; in particular, it has between 10 and 50 pairs (A-B-A-B- . . . structure) or triplets (A-B-C-A-B-C- . . . structure) of one anionic and one cationic layer former.

In layer structures studied in more detail by the inventors and expediently formed using commercially readily available compounds, polystyrene sulfonate (abbreviated PSS) or polystyrene sulfonate sodium salt (Na-PSS) are [sic] as layer formers or has [sic] poly-4-vinylbenzyl(N,N-diethyl-N-methyl) ammonium iodide as the anionic polyelectrolyte (compound A) and polyvinyl sulfonate or a polyvinyl sulfonate potassium salt or a polyallylamine or polyallylamine hydrochloride (PAH) as the cationic polyelectrolyte (compound B). In an advantageous triple layer, poly-(1-(4-(3-carboxy-4-hydroxyphenylazo) benzene sulfonamide)-1, 2-ethanediyl)sodium salt (PAZO) can be used as compound C.

The outermost layer may in particular have an uncharged polymer, such as polyethylene oxide or bisamino-polyethylene glycol.

Good adhesion of the organic layer and simultaneously high phase-boundary capacitance are advantageously attained with a version of the stimulation electrode in which the surface located under the organic layer has a pronounced surface roughness or porosity, so that the effective physisorption surface area is larger by at least one order of magnitude than the surface resulting from the geometrical basic shape of the stimulation electrode. A fractal surface geometry, with which the effective physisorption surface area can be increased by two to three orders of magnitude, compared with the surface area resulting from the geometrical basic shape of the stimulation electrode, is especially preferred. An electrode structure with advantageous properties is obtained, according to the investigations of the inventors, additionally if between the metal substrate body and the organic layer a nonmetallic layer, in particular a layer having carbon, carbide, nitride or carbonitride, is provided. A layer of iridium nitride or iridium oxide is usable as this layer; but alternatively an underlay layer of metallic iridium may also be provided.

The organic layer itself may have a first constituent layer that is in contact with the substrate body and that lends the adhesion thereto. This constituent layer may be adapted to the substrate body with respect to the reactivity. To achieve a specific functionalization—in particular for additional uses of the electrode—a compound selected suitably for the desired physiological effect is specifically bonded, in particular as a ligand, to the reactive groups. In special cases, however, both functions can also be realized in one homogeneous layer.

Features of major significance for the usual use of a stimulation electrode are those in which the outer surface of the organic layer is passivated relative to the nonspecific adsorption of bio-macromolecules—for instance by having polyethylene glycol—or in which it has means for controlling the wettability, in particular a compound having molecules with an OH, COOH or $NH_2$ terminal group for increasing wettability, or a compound having a $CH_3$ group or a perfluorinated alkyl chain, for reducing wettability.

The stimulation electrode according to the invention is suitably produced on the basis of electrodes or substrate bodies known per se, onto which the ultrathin organic layer is deposited by a gas phase reaction or from the solution. To assure a high adhesive strength, a contributing factor along with a choice of a suitable substrate in the sense of the specifications given above is—in the first case—that the gas phase reaction is performed in two steps; the second step is performed in a vacuum and at an elevated temperature compared to the first stage (physisorption from a material gas and/or covalent binding) to achieve a desorption of unreacted molecules, not fixed in the layer or to the surface (hydrolyzed molecules, small oligomers) from the organic layer deposited in the first step.

Prior to the gas phase reaction, dehydration of the surface of the substrate body—optionally also preceded by cleaning—may be expedient in order to promote a covalent bonding of the layer to the substrate, a process that would be hindered by water molecules.

Particularly for layers with specific functionalization, a two-stage method in a different sense is advantageous: In a first method step, a layer with reactive groups is deposited onto the surface of the substrate body, and in a second method step, a compound adapted to the desired physiological effect is covalently bonded to the reactive groups. The second stage may be within the context of the fabrication process in a narrower sense, but may also follow at the beginning of the use of the electrode in a special chemical environment—or in other words independently of the actual fabrication process. Since the electrode is functionally not finished until after this second stage, it can nevertheless be counted as part of the production process.

Advantageous further features of the invention are defined by the dependent claims and are described in further detail below in conjunction with the drawings, together with the description of the preferred embodiment of the invention. Shown are:

DESCRIPTION OF THE PREFERRED EMBODIMENT

Figure 1A:
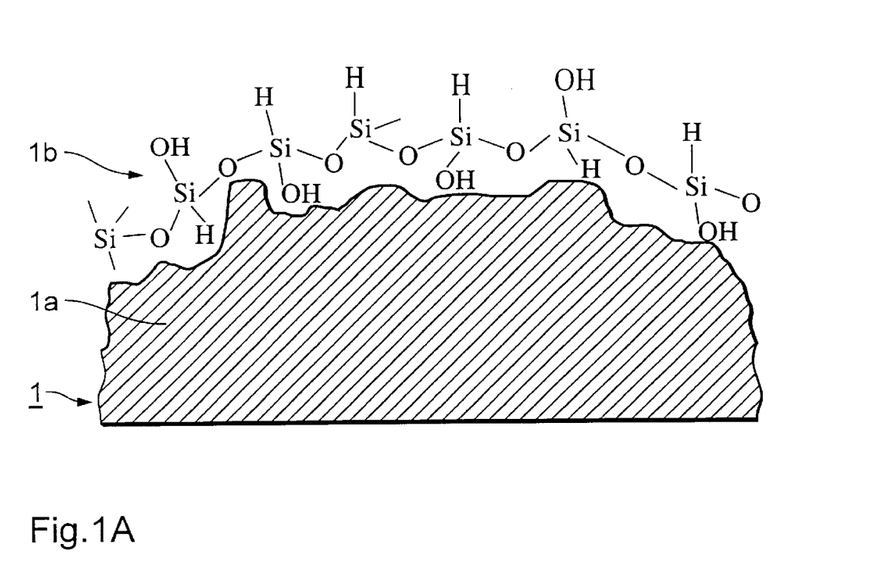
FIGS. 1a and 1b, a basic illustration to explain the construction of an implantable stimulation electrode in one embodiment of the invention.

FIG. 1a and [sic], in a basic illustration, shows the structure of an implantable stimulation electrode 1 with an iridium substrate 1a (shown in a fragmentary cross section) with a roughened surface and a laterally cross-linked, ultrathin polysiloxane layer 1b adsorbed on this surface.

The polymer layer 1b is created on the substrate body 1a, the latter being produced in the usual way, in a multistage vacuum/gas phase process in a heatable and evaluatable glass reactor. First, the surface of the cleaned substrate body is dewatered for one hour at 60° C.; then in a first reaction step—again at 60° C.—in an atmosphere containing argon and trichlorosilane as material gas, silylation of the surface is performed for 1 to 2 hours, and finally, in a second reaction step after evacuation of the reactor, the electrode is treated at 100 to 200° C., in order to achieve desorption of the molecules of the silylation agent, which in the first step have been merely physisorbed but not firmly bonded into the layer.

Figure 1B:
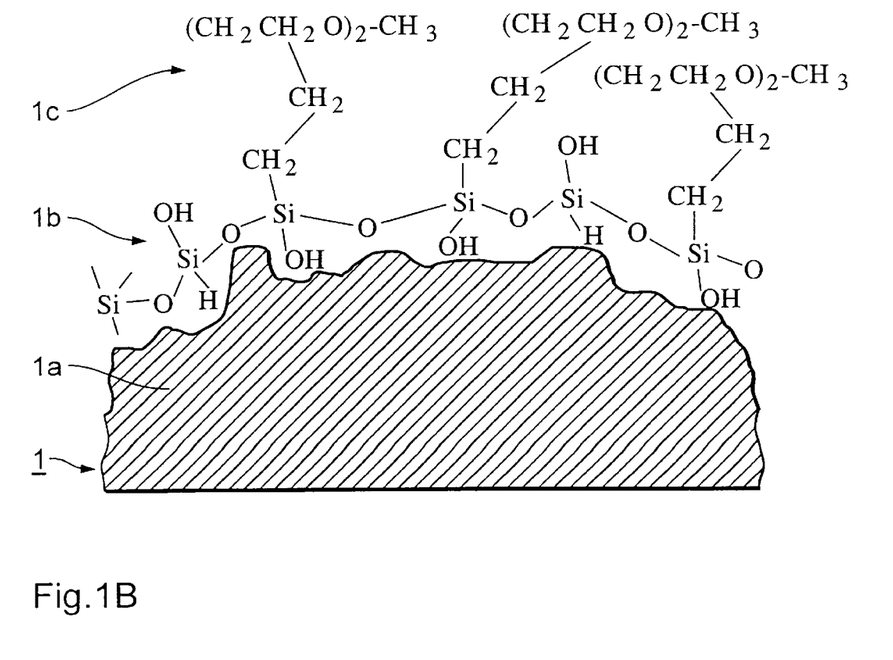

FIG. 1b shows the electrode functionalized by means of an additional polyethylene glycol (PEG) layer 1c. Instead of PEG, polyethylene oxide (PEO) can also be used here.

Figure 2:
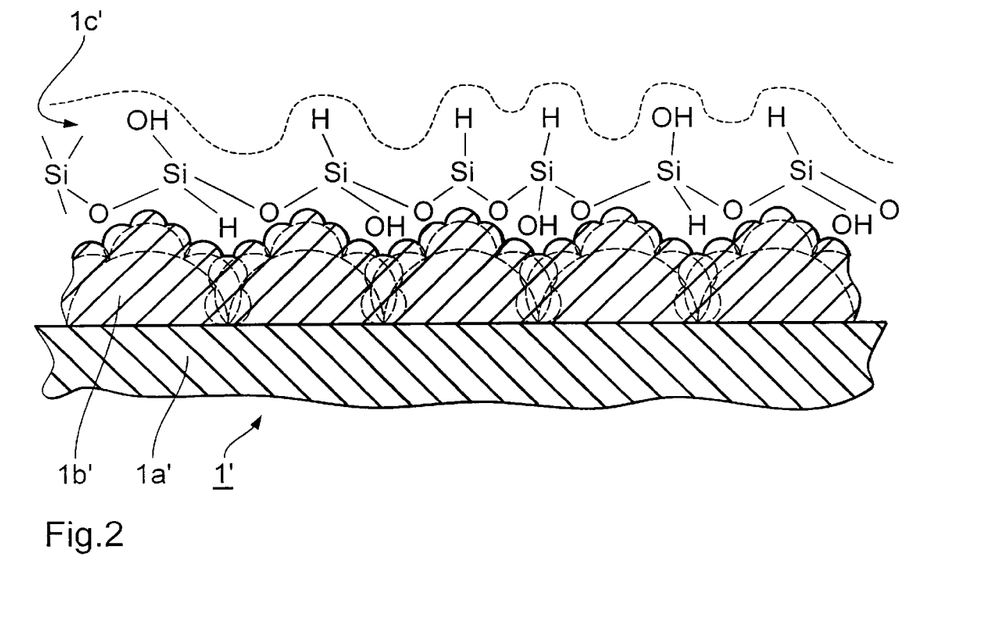
FIG. 2, a basic illustration of the construction of an implantable stimulation electrode in another embodiment.

FIG. 2 shows a basic illustration of a stimulation electrode 1' modified over FIG. 1 in the substrate body. Here, a titanium substrate 1a' with a smooth surface is first provided, by means of a preceding gas phase process, with an iridium layer 1b' with a fractal surface geometry; it offers a very large adsorption surface area for the polysiloxane layer 1c', subsequently applied (approximately in the way described above) as an adhesion layer. A functionalizing layer may be provided analogously to FIG. 1B.

Especially advantageous electrical properties and pronounced biocompatability are obtained, according to investigations of the inventors, by means of derivatization with polyethylene glycol-terminated molecules, for instance by providing the polysiloxane layer also with (1) an alkyl epoxy and finally a bisamino-polyethylene glycol, or (2) with an allyl-PEG layer.

Figure 3A:
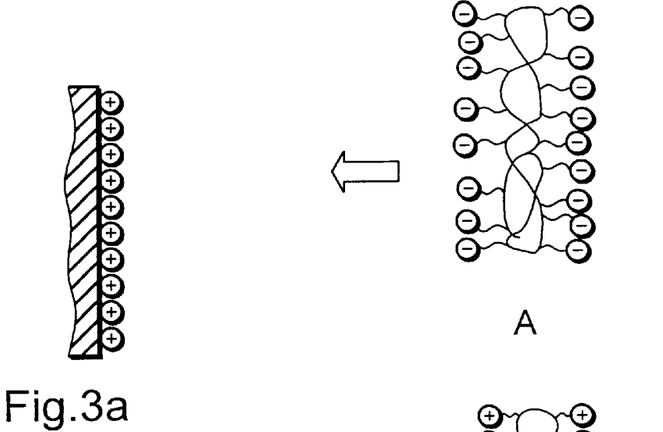
FIGS. 3a–3c, a basic illustration of the construction of a polyelectrolyte multilayer in a further embodiment of the invention.
Figure 3B:
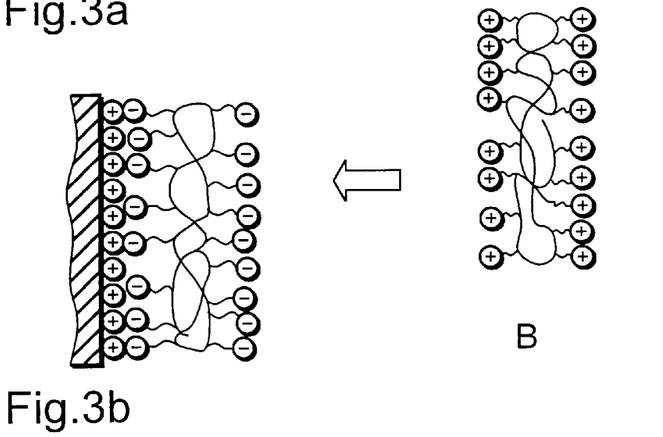
Figure 3C:
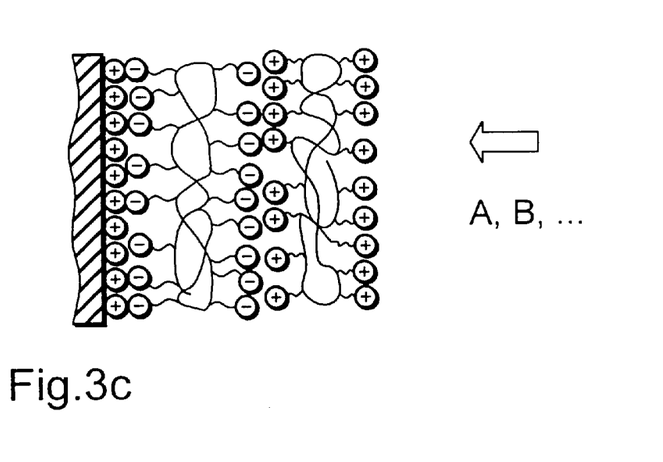

FIGS. 3a–3c—in highly simplified graphic illustration of the compounds, which is not intended to reproduce their actual three-dimensional structure in the solution or after the adsorption—show a basic view of the first steps in the construction of a polyelectrolyte multilayer as an organic layer, in a further embodiment.

Adhering to a metal surface, occupied (for instance by means of cysteamine with positive surface charges is first—as shown in FIGS. 3a and 3b—for instance upon immersion in a solution of poly(styrene sulfonate)-sodium salt (M=100,000, concentration $1.01 \cdot 10^{-2}$ monomol/l, NaCl concentration approximately 2.0 mol/l) is polystyrene sulfonate (PPS) [sic] as an anionic polyelectrolyte A, whose layer thickness after about 20 minutes is 45 A (4.5 nm). After being washed off with high-purity water, the substrate is immersed in a second solution with poly(allyl amine) hydrochloride (M=50,000 to 65,000, concentration $1.05 \cdot 10^{-2}$, NaCl concentration approximately 2.0 mol/l), which contains the cationic polyelectrolyte poly(allyl amine) (PAH), which adheres as compound B—as shown in FIGS. 3b and 3c. After about 20 minutes, the layer thickness here is approximately 7 A (0.7 nm). An AB pair or a repeating unit of the adsorbed structure accordingly has a "lattice constant" of something over 50 A (5 nm), which was confirmed by investigating the small-angle X-ray scattering. Repetitions of the immersion operations analogously lead to the adsorption of further layers A and B or further repeating units. In the investigations performed by the inventors, layer numbers between 30 and 40 prove to be practicable. The individual layer thicknesses can be controlled as needed via the addition of salt.

As compound A, poly(vinyl sulfate) (PVS) was also successfully used as a sodium salt (M=245,000), resulting in a pair layer thickness of approximately 13.5 A (1.35 nm)—with special adjustment of the solution using PAH, for instance. Combined layer structures, for instance comprising a plurality of PSS/PAH pairs and then a few PVS/PAH pairs, are also feasible in an advantageous version of the invention.

In a modified method course, poly-(1-(4-(3-carboxy-4-hydroxyphenylazo) benzene sulfonamide)-1,2-ethanediyl)-sodium salt (PAZO)—in fundamentally the same way as described above—is also used as the third compound C in the form of sodium salt (concentration $9.8 \cdot 10^{-3}$ monomol/l, NaCl concentration 0.1 mol/l). The repeating unit here is consequently a triplet ABC.

Figure 4A:
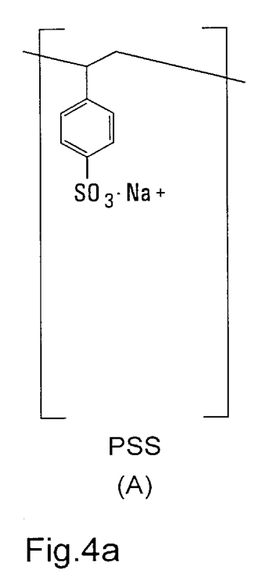
FIGS. 4a–4c, schematically, the chemical structure of some compounds that are used in polyelectrolyte multilayers of FIG. 3.
Figure 4B:
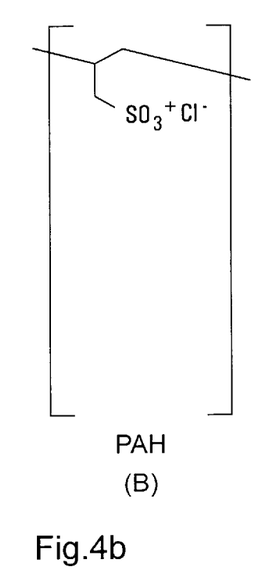
Figure 4C:
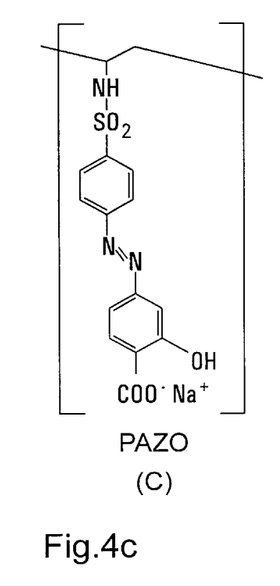

FIGS. 4a–4c schematically show the chemical structure of the aforementioned compounds that are used in polyelectrolyte multilayers of FIG. 3, [sic]

Figure 5:
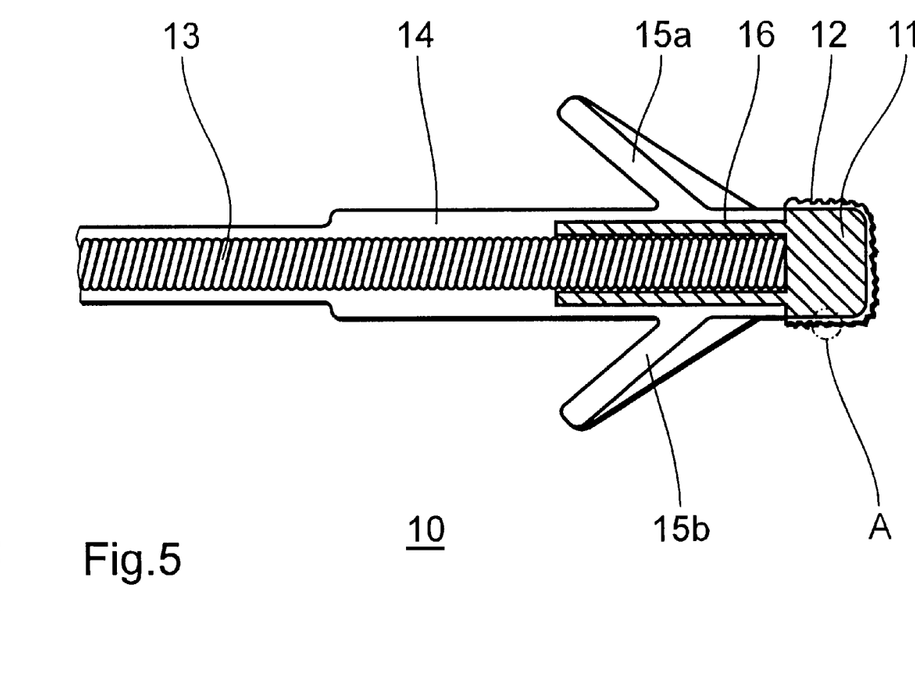
FIGS. 5 and 5a, a schematic cross-sectional view of the distal end of a unipolar polyelectrolyte electrode line, with an electrode head, in accordance with one embodiment of the invention.
Figure 5A:
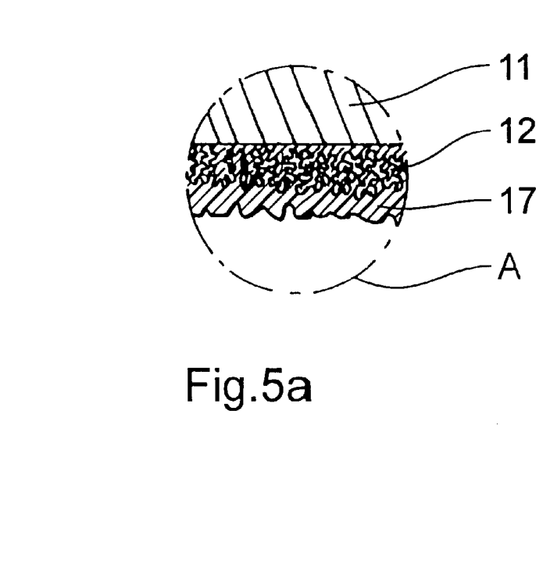

FIGS. 5 and 5a, in a schematic cross-sectional view, show the distal end of a unipolar pacemaker electrode line 10. This is a unipolar button electrode with a head that has a cylindrical titanium base body 11. The cylindrical base body 11 has a surface coating 12 of iridium nitride (IrN), which is applied to the base body by cathode atomization (reactive sputtering). The electrode has a coiled electrically conductive supply lead 13, which is provided with an electrically insulating sheathing 5 of silicone. Formed onto the silicone sheathing are flexible fastening elements (fins) 15a and 15b, oriented rearward (proximally), which serve to fix the electrode in the heart; the surface of the base body is kept in contact with the inside wall of the heart. The base body 11 is thrust over the supply lead 13 by means of a hollow-cylindrical attachment piece 16 and secured there.

FIG. 5a shows an enlarged detail (detail A in FIG. 1) of the active surface. As can be seen from this drawing, a substantial enlargement of the active surface area is attained by the fractal three-dimensional geometry (enlarged not to scale) of the coating 12, which has grown in columnar or cauliflower-like form in the microscopic range. The surface area enlargement attained, because of a suitable choice of method parameters in the sputtering process, amounts to from two to more than three orders of magnitude, compared with the surface area of a smooth cylinder having the same dimensions as the base body 11. An organic layer 17 with a layer thickness of a few nanometers is adsorbed onto the IrN coating 12 by one or [sic] above-described methods, which practically does not impair the electrical properties of the coating 12 but has a markedly positive effect on the course of stimulation threshold during the growth of the electrode 10 on the heart wall.

By way of example, the layer may be an SiH+allyl glycidyl ether+bis-aminoPEO layer, produced by the two-stage method, for instance, that is formed as follows:

A batch of electrodes coated fractally with iridium is subjected to ultrasound for 5 to 10 minutes with high-purity water and blown dry with argon. In a gas phase reactor, the electrodes are dried for 30 minutes at 60° C. and p=0.1–1 mbar before trichlorosilane is vapor deposited at 60 to 90° C. The electrodes are incubated for 60 to 120 minutes in the trichlorosilane atmosphere. After that, the delivery of trichlorosilane is discontinued and evacuation is done, so that only physisorbed material is desorbed. ESCA is used to demonstrate that this process creates a polysiloxane network on the iridium electrode. This network is firmly bonded to the electrode and withstands even further reaction steps in organic solvents at elevated temperature.

The electrodes coated with a polyhydrogen siloxane network are placed in a flask in argon. 100 ml of allyl glycidyl ether and 0.5 ml of a Lamoreaux catalyst, containing 3% platinum, are added drop by drop. The mixture is heated for 8 h to 100° C.; the fixation of the allyl glycidyl ether to the surface takes place with Si—C bond linkage. Once the reaction ends, the electrodes are rinsed off with methanol. Next, the electrodes are heated for 10 h to reflow temperature in a solution of 100 ml of methanol and 10 g of O,O-bis(2-aminopropyl)polyethylene glycol (molecular weight approximately 1900 g/mol). The electrodes are then rerinsed with methanol.

Figure 6:
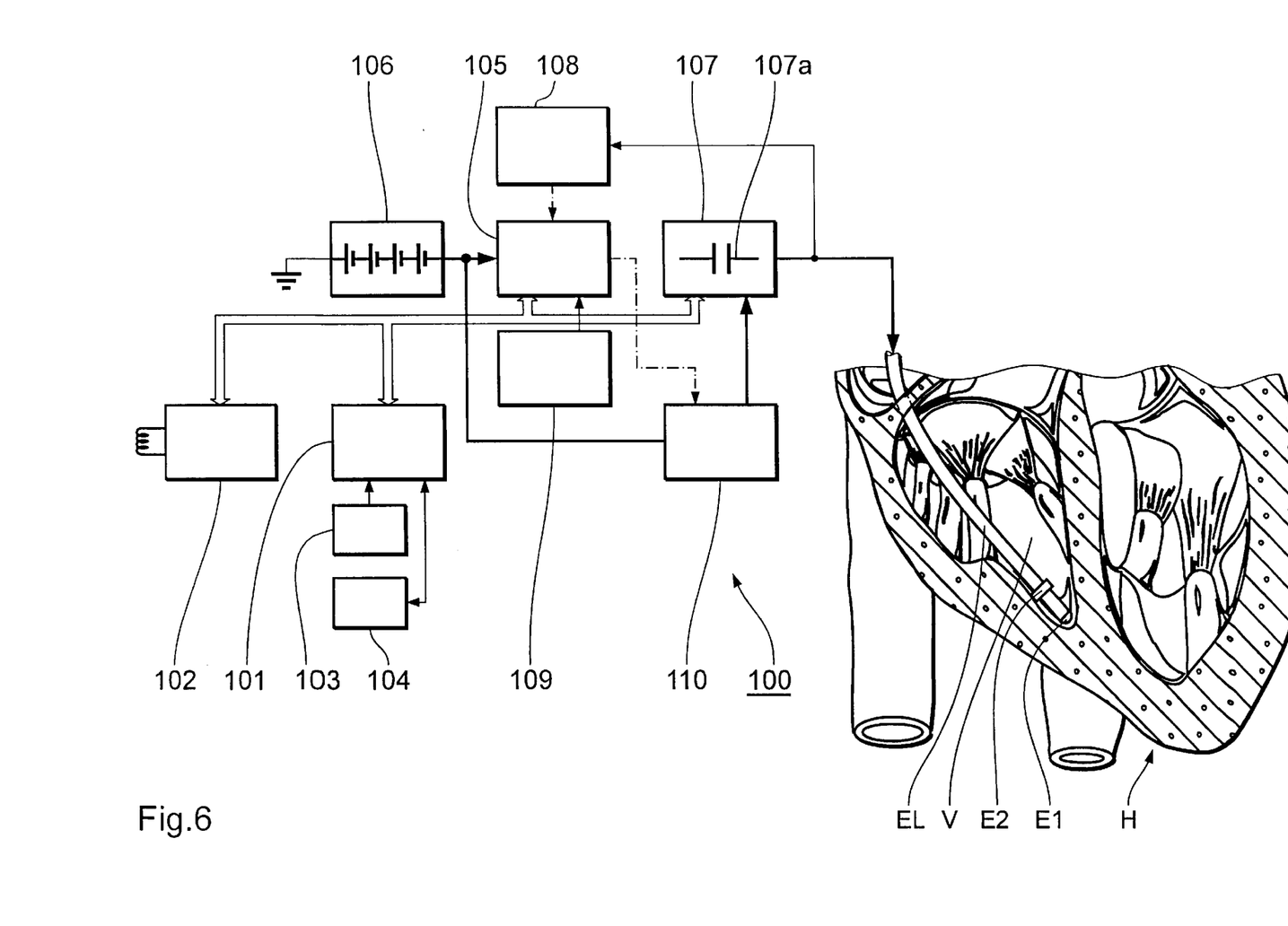
FIG. 6, a basic illustration of a bipolar pacemaker electrode arrangement, in which a version of the stimulation electrode of the invention is used.

FIG. 6—again in a highly simplified illustration—shows a single-chamber demand pacemaker 100, which is connected via a bipolar electrode line EL, which has a tip electrode E1 and a ring electrode E2, to the right chamber V of a heart H, on the one hand in order to sense natural heart actions and on the other for the demand-related emission of stimulation pulses.

The essential control component groups of the pacemaker 100 shown are a microprocessor 100, with which a telemetry unit 102 and a program memory 103 and a data memory 104 are associated in the usual way, and a controller/timing unit 105. A lithium battery 106 serves to supply electrical current to the pacemaker components and delivers stimulation energy to an output stage 107 via a pump control circuit 110. The output stage—as represented by the capacitor 107a—includes a storage capacitor array for storing electrical energy in order to attain a stimulation amplitude that is elevated compared with the battery voltage. A data and control signal bus is shown between the microprocessor 101, the telemetry unit 102, the controller/timing unit 105 and the output stage 107. Connected in the usual way to the electrodes E1 to E2 is an input stage 108, which is in data signal communication with a control input of the controller/timing unit 105. This unit is also assigned an oscillator circuit 109 on the input side. On the output side, the controller/timing circuit is connected—in addition to the connections realized via the bus line—to a control input of the pump control circuit 110. The generation and emission of stimulation pulses and most of the other sequences of operation are controlled in this arrangement in a manner known per se, so that this requires no special explanation here.

The embodiment of the electrodes E1, E2 with an organic layer in accordance with the specifications given above enables pacemaker operation with substantially constant sensing sensitivity and stimulation energy, even during the period while the tip of the electrode line EL is growing into the heart wall. The organic coating prevents the occurrence of tissue irritation or inflammation, which in conventional electrodes can cause considerable temporary increases in the stimulation threshold. As a result, readjustments of the sensing amplification and/or the stimulation amplitude can be omitted and the pump current—and hence battery consumption—in this phase is reduced, with the overall result being simplified use and a longer service life of the pacemaker.

The possibility also exists, by incorporating charged biological molecules into the organic coating—especially as a "substitute" for one or more layers in a polyelectrolyte multilayer or by covalent bonding to reactive groups of the layer via side groups of the molecules—of realizing a biological-physiological function and at the same time securely immobilizing the applicable molecules.

Figure 7:
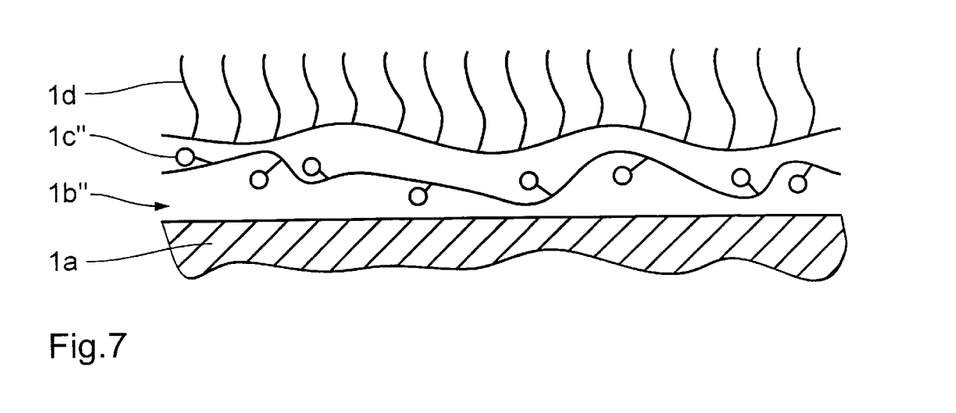
FIG. 7, a basic illustration of a sensor electrode according to a further embodiment of the invention, and FIG. 8, a basic illustration of an anti-inflammatory electrode in accordance with a further embodiment of the invention.

This is sketched as an example in FIG. 7, in which reference numeral $1a$ again indicates the substrate body, $1b''$ an adhesive layer, $1c''$ enzyme molecules, for instance, and $1d$ a PEG termination layer. One example of this is the incorporation of glucose oxidase to achieve an amperometric biosensor electrode for determining glucose.

Figure 8:
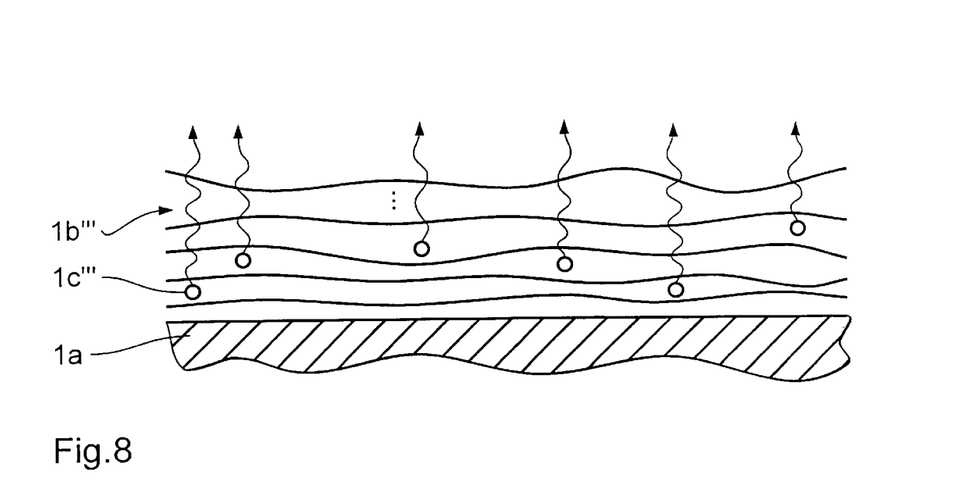

Another possible functionalization is shown in FIG. 8, which in the form of a basic sketch shows the incorporation of an anti-inflammatory active ingredient $1c'''$ (known per se) into a relatively thick polyelectrolyte multilayer with a high dielectric constant $1b'''$ on an electrode surface $1a$. The departure of the active ingredient from the organic layer functioning as a deposit is diffusion-controlled—as symbolically indicated by the arrows.

The invention is not limited in its embodiment to the exemplary embodiments given above. Many variants are conceivable that make use of the fundamental concept of the invention as described even in different types of versions.

We claim:

1. An implantable stimulation electrode ($1$; $1'$; $10$; E1, E2) for use with an implantable tissue stimulator ($100$), in particular a pacemaker, defibrillator, bone or neurostimulator, having a metal substrate body ($1a$, $1a'$; $11$) and a coating ($1b$; $1b'$, $1c'$; $1b''$, $1d$; $1b'''$; $12$, $17$), applied to the substrate body, for reducing the electrode impedance and/or increasing the tissue compatability, characterized in that
   a thin, specifically functionalized organic coating ($1b$; $1c'$; $1b''$, $1d$; $1b'''$; $17$) forming the entire outer surface of the stimulation electrode is provided, which adheres firmly to the underlying surface as a consequence of irreversible physisorption or covalent chemical bonding.

2. The implantable stimulation electrode of claim 1, characterized in that the organic coating ($1b$; $1c'$) has a polymeric network structure formed by substantially lateral polymerization.

3. The implantable stimulation electrode of claim 1, characterized in that the organic coating has a multilayer structure ($1b'''$) formed by successive adsorption of one anionic and one cationic polyelectrolyte (A, B).

4. The implantable stimulation electrode of claim 3, characterized in that the medicinal active ingredient ($1c'''$) is substantially embedded between constituent layers of the multilayer structure ($1b'''$).

5. The implantable stimulation electrode of claim 3, characterized in that the organic coating has between 2 and 50 pairs or triplets of one anionic and one cationic layer former.

6. The implantable stimulation electrode of claim 3, characterized in that the organic coating has alternating layers A of polystyrene sulfonate or polystyrene sulfonate sodium salt, or poly-4-vinylbenzyl (N,N-diethyl-N-methyl) ammonium iodide and B comprising polyvinyl sulfonate or polyvinyl sulfonate potassium salt, or a polyallylamine or polyallylamine hydrochloride.

7. The implantable stimulation electrode of claim 3, characterized in that the organic layer ($1b$; $1b'''$) is terminated on the outer surface by an uncharged polymer ($1c$; $1d$), in particular polyethylene oxide or polyethylene glycol.

8. The implantable stimulation electrode of claim 7, characterized in that the sensor molecules ($1c''$) are embedded in the organic layer substantially underneath the uncharged polymer ($1d$).

9. The implantable stimulation electrode of claim 1, characterized in that the organic layer ($1b''$) has sensor molecules ($1c''$), in particular enzyme molecules, in such a way that the stimulation electrode can act as a biosensor electrode.

10. The implantable stimulation electrode of claim 1, characterized in that the organic layer ($1b'''$) has a medicinal active ingredient ($1c'''$), in particular an anti-inflammatory medication, which can be exported from the organic layer by diffusion control or solution control.

11. The implantable stimulation electrode of claim 1, characterized in that the layer thickness of the organic coating is in the range between 1 and 200 nm.

12. The implantable stimulation electrode of claim 1, characterized in that the organic coating has a relative dielectric constant of greater than 100, and in particular greater than 300.

13. The implantable stimulation electrode of claim 1, characterized in that the underlying surface has a surface roughness or surface porosity such that the effective physisorption surface area is larger by at least one order of magnitude than the surface resulting from the geometrical basic shape of the stimulation electrode.

14. The implantable stimulation electrode of claim 1, characterized in that the underlying surface has a fractal surface geometry such that the effective physisorption surface area is greater by two to more than three orders of magnitude than the surface area resulting from the geometric basic shape of the stimulation electrode.

15. The implantable stimulation electrode of claim 1, characterized in that a nonmetallic layer ($12$), in particular a layer having carbon, an oxide, carbide, nitride or carbonitride, is provided between the metal substrate body ($11$) and the organic coating ($17$).

16. The implantable stimulation electrode of claim 1, characterized in that between the metal substrate body ($1a'$; $11$) and the organic layer ($1c'$; $17$), a layer ($1b'$; $12$) of iridium, iridium nitride or iridium oxide is provided.

17. The implantable stimulation electrode of claim 1, characterized in that the organic coating has a nonorganic polymeric constituent layer ($1b$), in particular a polysiloxane layer.

18. The implantable stimulation electrode of claim 1, characterized in that the organic layer has reactive groups, to which at least one compound adapted to a desired physiological function, in particular as a ligand, is specifically bonded.

19. The implantable stimulation electrode of claim 1, characterized in that the outer surface ($1c$; $1d$) of the organic layer effects a passivation with respect to an adsorption of biological macromolecules and cells.

20. The implantable stimulation electrode of claim 1, characterized in that the outer surface of the organic layer has a compound for controlling the wettability, in particular a compound having a molecule with an OH, COOH or $NH_2$ terminal group for increasing the wettability, or a compound having a $CH_3$— group or a perfluorinated alkyl chain for reducing the wettability.

* * * * *